(12) United States Patent
Koh

(10) Patent No.: US 7,894,901 B1
(45) Date of Patent: Feb. 22, 2011

(54) APPARATUS AND METHOD FOR ASSESSING CARDIAC THERAPY

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 939 days.

(21) Appl. No.: 11/466,074

(22) Filed: Aug. 21, 2006

(51) Int. Cl.
*A61N 1/365* (2006.01)

(52) U.S. Cl. .............................. 607/19; 607/27; 607/28

(58) Field of Classification Search .................. 607/27, 607/19; 600/509, 513
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Man et al. | |
| 4,944,298 A | 7/1990 | Sholder | |
| 5,370,667 A * | 12/1994 | Alt | 607/19 |
| 5,466,254 A | 11/1995 | Helland | |
| 5,476,483 A | 12/1995 | Bornzin et al. | |
| 6,361,501 B1 * | 3/2002 | Amano et al. | 600/500 |
| 6,408,207 B1 | 6/2002 | Hastings et al. | |
| 6,539,249 B1 * | 3/2003 | Kadhiresan et al. | 600/510 |
| 6,643,549 B1 * | 11/2003 | Bradley et al. | 607/28 |
| 2004/0210261 A1 * | 10/2004 | King et al. | 607/9 |
| 2005/0267542 A1 * | 12/2005 | David et al. | 607/17 |

* cited by examiner

*Primary Examiner*—Carl H Layno
*Assistant Examiner*—Natasha N Patel

(57) ABSTRACT

A patient's response to therapy such as CRT is assessed by cross correlation of a patient's evoked response and physical activity surrogates. Based on the cross correlation, a determination may be made as to whether or how much the therapy is helping the patient's physical activity. For example, the degree of cross correlation index between IEGM parameters and activity threshold parameters may be used to assess whether the patient's heart condition improves the patient's physical activity. The therapy may then be modified as necessary in the event the patient is not sufficiently responding to the therapy.

20 Claims, 7 Drawing Sheets

APPARATUS AND METHOD FOR ASSESSING CARDIAC THERAPY

TECHNICAL FIELD

This application relates generally to implantable cardiac stimulation devices and, in some embodiments, to an apparatus and/or method for assessing cardiac therapy.

BACKGROUND

When a person's heart does not function normally due to, for example, a genetic or acquired condition, various treatments may be prescribed to correct or compensate for the condition. For example, pharmaceutical therapy may be prescribed for a patient or a pacemaker may be implanted in the patient to improve the function of the patient's heart.

In patients with severe heart problems cardiac resynchronization therapy ("CRT") may be prescribed. Briefly, CRT involves attempting to resynchronize the actions of the chambers of the heart. Thus, CRT may be prescribed for patients with significant atrioventricular mechanical dys-synchrony ("DYS"), interventricular mechanical DYS, or intraventricular mechanical DYS. As an example, a bundle branch block may disrupt the normal synchronized depolarization of the left and right ventricles. CRT may attempt to address this problem by, for example, pacing the left and right ventricles at substantially the same time.

One central issue in CRT is identification of patients most likely to respond to the therapy. Conventionally, a wide QRS complex has been correlated with mechanical ventricular DYS. Accordingly, a significant percentage of the controlled studies on CRT have been conducted on patients suffering from congestive heart failure that have a wide QRS complex.

While the above correlation may be correct in some instances, it is not true in all cases. For example, some patients with a wide QRS complex do not have marked mechanical ventricular DYS. Conversely, some patients with a normal or narrow QRS complex may still suffer from significant mechanical DYS and, hence, are candidates for CRT. Moreover, a surface ECG measured for CRT assessment may not be accurate since the ECG is affected by the insulted location of the heart. Also, although some short-term experimental studies have shown that patients with wider QRS complexes have a greater immediate mechanical response to CRT, a significant percentage of long-term studies have shown that QRS complex duration does not predict a response to CRT. In addition, narrowing of the QRS complex may not predict a functional improvement following CRT. Furthermore, some CRT recipients may experience a worsening of symptoms and mechanical DYS. In summary, a significant percentage of patients selected for CRT based on QRS complex duration as a surrogate for mechanical ventricular DYS may not respond to the therapy.

Moreover, some methods for determining whether a patient is responding to CRT are relatively expensive. For example, a series of relatively expensive echocardiogram procedures may be used to measure any changes in the patient's cardiac output over time. Such a procedure is typically performed by a doctor in the doctor's office or a clinical setting, further adding to the overall cost. Furthermore, such a procedure may not reflect real-time conditions such as when the patient is exercising or walking up a flight of stairs.

SUMMARY

A summary of various aspects and/or embodiments of an apparatus constructed or a method practiced according to the invention follows. For convenience, an embodiment of an apparatus constructed or a method practiced according to the invention may be referred to herein simply as an "embodiment."

The invention relates in some aspects to assessing cardiac therapy. For example, in some embodiments an apparatus is provided and/or a method is provided for assessing CRT.

In some embodiments a patient's response to CRT therapy is assessed by cross correlation of a patient's evoked response and physical activity surrogates. For example, data relating to these two parameters may be collected over time. The data may then be cross correlated to identify any trends over time. In this way, a determination may be made as to whether the therapy's effect on the patient's heart condition has a positive impact on the patient's physical activity.

Various parameters relating to a patient's evoked response may be collected for use in the cross correlation operation. Typically, the evoked response is indicated by intracardiac electrogram ("IEGM") morphology-derived parameters collected by an implantable cardiac device. For example, the process may involve collecting peak-to-peak ("P-P") values of the IEGM signal, paced depolarization integral ("PDI") data, slope values associated with the IEGM signal or other suitable data.

Various parameters relating to a patient's activity (physical activity surrogates) may be collected for use in the cross correlation operation. For example, the process may involve collecting data from an accelerometer, a pressure sensor, physically observed parameters or other suitable data.

In some embodiments the evoked response and activity parameters may be collected periodically (e.g., daily) over a given period of time (e.g., one month) at which time a cross correlation is performed on the collected parameters. This process may be repeated (e.g., every month) to obtain a series of cross correlation values. The cross correlation values may then be assessed to generate an indication as to the patient's response to CRT. For example, the cross correlation values may be analyzed to identify a trend (e.g., better, worse, or no change). Based on this indication, the patient's therapy may be modified (e.g., timing intervals adjusted).

BRIEF DESCRIPTION OF THE DRAWINGS

These and other features, aspects and advantages of the invention will be more fully understood when considered with respect to the following detailed description, appended claims and accompanying drawings, wherein:

Figure 1:
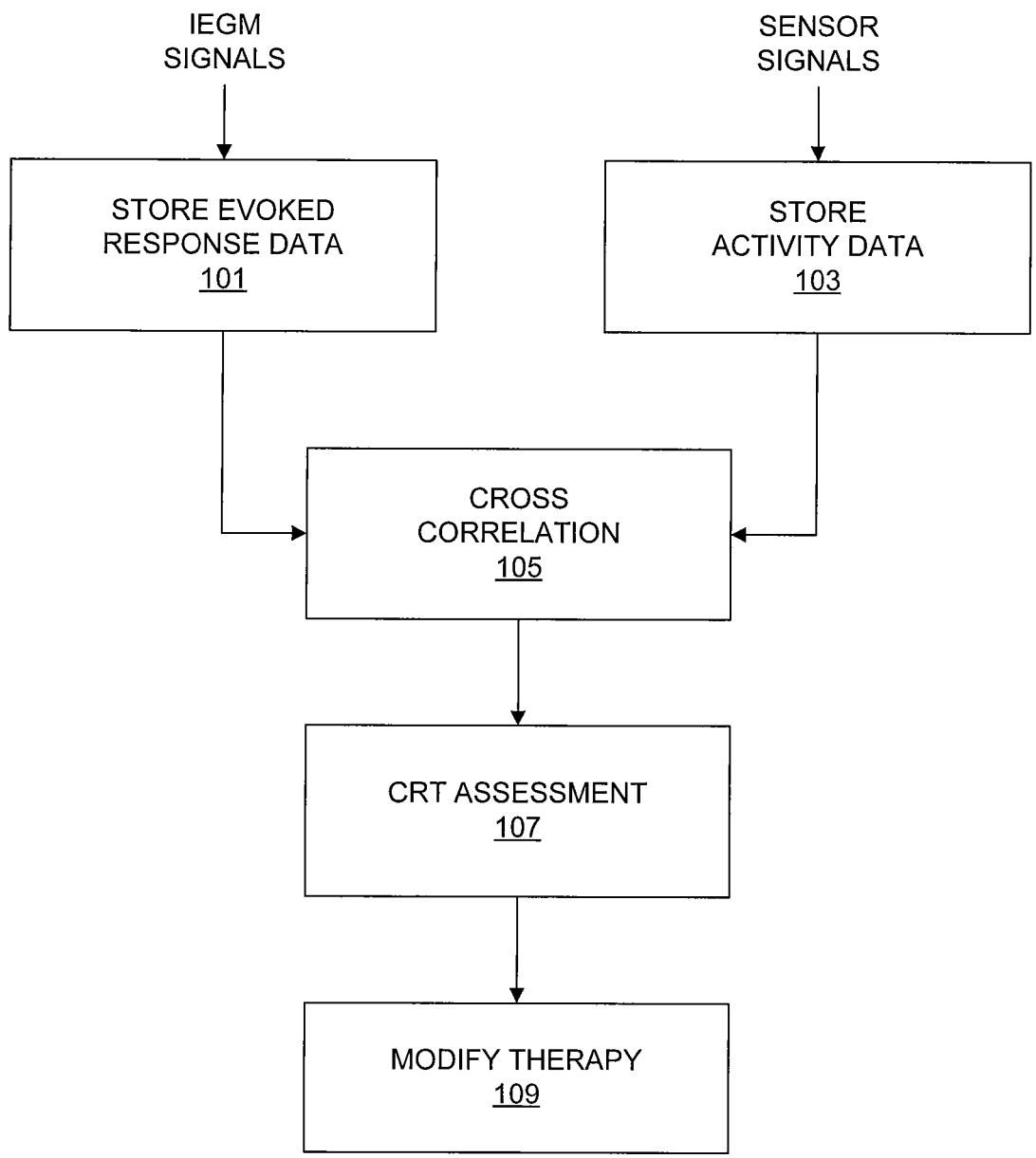
FIG. 1 is a simplified diagram of one embodiment of operations that may be performed in conjunction with assessment of cardiac therapy such as CRT.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may appear to be quite different from those of the disclosed embodiments. Consequently, the specific structural and/or functional details disclosed herein are merely representative and do not limit the scope of the invention. For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented and/or a method practiced using other structural and/or functional details in addition to or other than the structural and/or functional details set forth in any disclosed embodiment(s). Accordingly, references to "an" or "one" embodiment in this discussion are not necessarily to the same embodiment, and such references mean at least one embodiment.

The invention relates in some aspects to an apparatus and/or method for assessing the effectiveness of cardiac therapy such as CRT that has been prescribed for a patient. Based on such an assessment, a determination may be made as to whether the patient is responding to the therapy. In conjunction with this, a determination may be made as to whether the CRT parameter settings are adequate for the patient and/or whether the patient is in the correct classification.

Some embodiments involve assessing CRT by cross correlation of physical parameters associated with the patient. For example, evoked response information obtained by sensing the cardiac activity of the patient may be cross correlated with activity information obtained by sensing and/or observing the physical activity of the patient.

Referring to FIG. 1, in some embodiments an apparatus may be configured to acquire IEGM signals indicative of the cardiac activity and sensor signals indicative of the physical activity. As represented by blocks 101 and 103, respectively, the apparatus may be configured to store evoked response data generated in accordance with the IEGM signals and to store activity data generated in accordance with the sensor signals. As will be discussed in more detail below, in some embodiments an implantable cardiac device and associated components may be adapted to sense cardiac activity and generate the IEGM signals and an implantable sensor may be used to sense motion of or physiologic conditions in the patient to generate the sensor signals. Typically, the apparatus is adapted to repeatedly (e.g., periodically) store the evoked response data and the activity data to generate a series of data for the cross correlation operation. For example, the data may be generated and stored on a daily basis (e.g., once a day).

As represented by block 105, the apparatus cross correlates the stored evoked response data and activity data at some later point in time. In some embodiments the apparatus is configured to repeatedly (e.g., periodically) perform the cross correlation to generate a series of cross correlation data. For example, the cross correlation may be performed on a monthly basis (e.g., once a month) on the data that was stored over the last month (e.g., at blocks 101 and 103). This procedure may then be repeated (e.g., over a three or six month period) to generate the series of cross correlation data.

As represented by block 107, the cross correlation of the evoked response data and the patient activity data may then be assessed. For example, the series of cross correlation data generated at block 105 may be evaluated to determine whether the values are trending up or down or are unchanged. Based on such an assessment, an indication may be generated as to whether, in response to the prescribed therapy, the condition of the patient has improved, worsened or remained the same.

Figure 2:
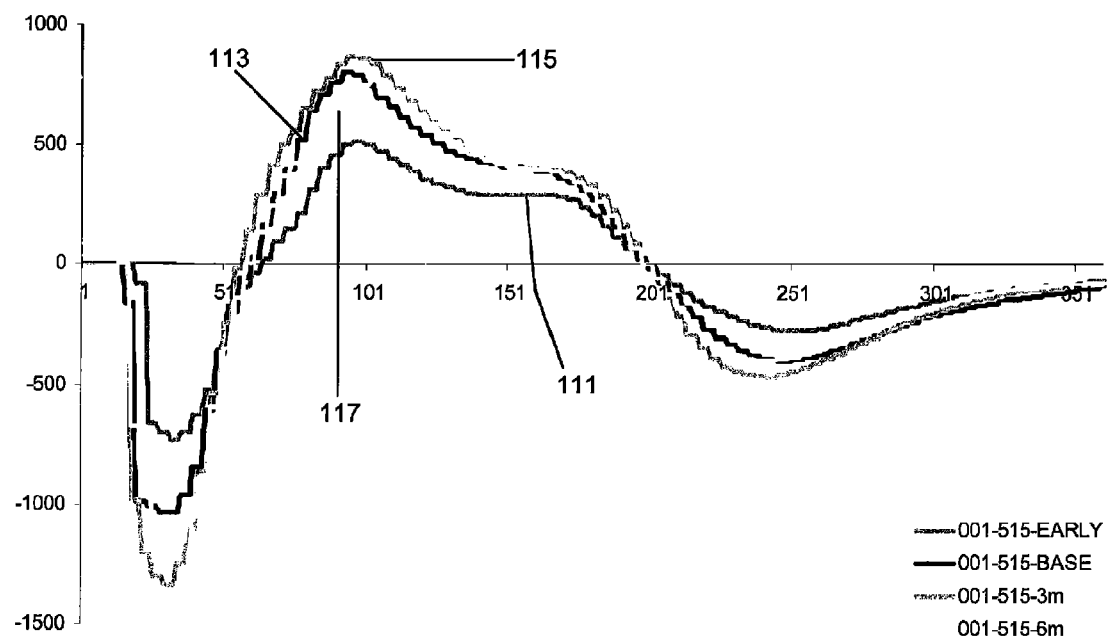
FIG. 2 is a simplified graph of an IEGM illustrating an example response to CRT.
Figure 3:
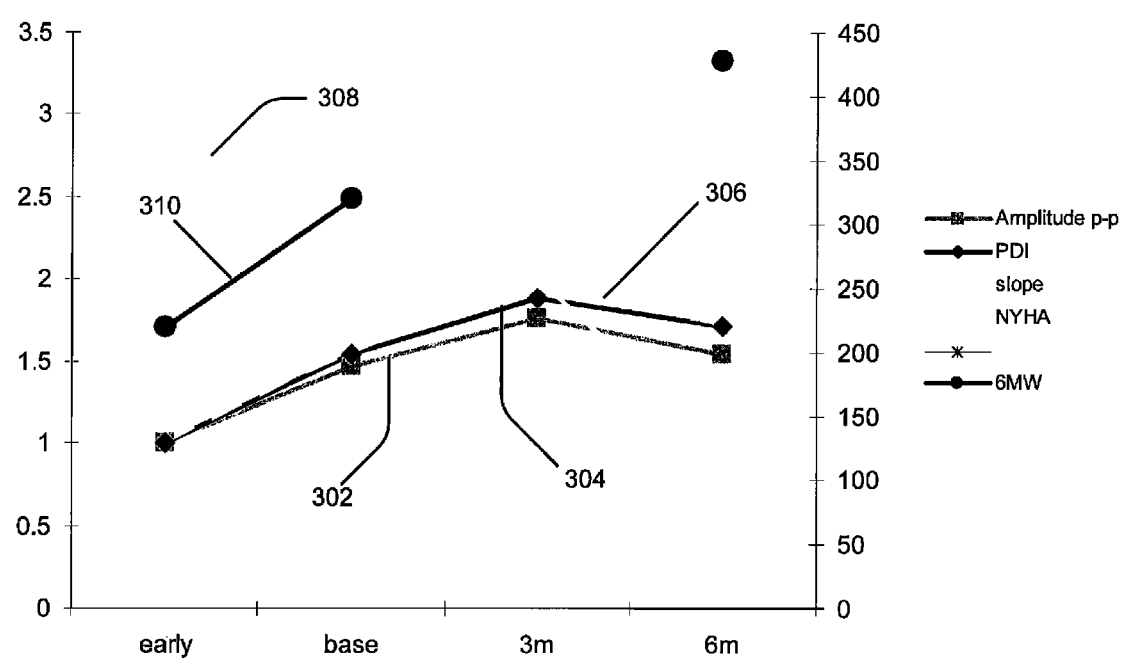
FIG. 3 is a simplified graph of various parameter illustrating an example response to CRT.

FIGS. 2 and 3 illustrate several examples of patient parameters that may serve as indicators of cardiac or physical performance. In addition, these figures illustrate how these parameters may change in response to CRT by depicting different values of the parameters for four different points in time. The first point in time may correspond to a time prior to commencement of CRT (designated "early"). The second point in time may correspond to a time shortly after commencement of CRT (designated "base"). The third point in time may correspond to a time (e.g., 3 months) after commencement of CRT (designated "3 m"). The fourth point in time may correspond to a later time (e.g., 6 months) after commencement of CRT (designated "6 m"). Parameters such as these may be cross correlated to provide an indication as to how a prescribed therapy is helping a patient's daily activity.

In FIG. 2 four representative IEGM signals 111, 113, 115 and 117 are shown with each signal corresponding to one of the four time periods, early, base, 3 m and 6 m, respectively. FIG. 2 illustrates that the peak-to-peak value of the IEGM signal may increase over time in response to CRT. For example, the peak-to-peak value of the signal 115 is greater than the peak-to-peak values of the signals 111 and 113. Here, an increase in peak-to-peak value may serve to indicate that CRT has improved the patient's cardiac performance.

FIG. 2 also illustrates that a slope of an IEGM signal may increase in response to CRT. For example, the slope (e.g., between x-axis points 51 and 101) of the signal 115 is greater than the corresponding slopes of the signals 111 and 113. Such an increase in slope also may serve as an indication that CRT has improved cardiac performance.

FIG. 3 summarizes these relationships along with similar relationships for other patient parameters for the four points in time (early, base, 3 m and 6 m). Curve 302 represents peak-to-peak values of an IEGM. Curve 306 represents slope values of an IEGM.

Curve 304 represents paced depolarization integral ("PDI") values. In general, PDI is the integral of the ventricular endocardial evoked response. In other words, PDI may represent an area under a curve corresponding to a time period between an atrium pacing pulse and a ventricle pacing pulse in an IEGM signal. Accordingly, an increase in PDI (e.g., as indicated by the value at 3 m as compared to the values at early and base) may serve as an indication that CRT has improved cardiac performance.

FIG. 3 also depicts several parameters that may provide an indication relating to the ability of a patient to perform physical activity. Parameters such as these may be derived, for example, by observing the patient and/or measuring certain physical conditions.

Curve 308 represents parameters associated with the New York Heart Association ("NYHA") classification system. In general, a NYHA classification of a patient involves observing certain physical attributes of the patient and generating a score (e.g., a class rank) based on the observation. For example, the patient may be observed while walking a long distance or climbing stairs, and the effect of that activity on the patient may be used to classify the patient. A lower NYHA score may indicate an improvement in physical activity.

Curve 310 represents a value associated with a six minute walk ("6 MW") for three of the points in time (early, base and 6 m). For example, the value may be a distance the patient is able to travel during a six minute walk. Accordingly, a longer distance may indicate an improvement in physical activity.

In patients who have responded positively to CRT, there may be a relatively strong correlation between an evoked response parameter (e.g., peak-to-peak value, PDI or slope value) and an activity parameter (e.g., physically observed parameters such as NYHA and 6 MW or other parameters discussed herein). Accordingly, cross correlation of evoked response parameters and activity parameters may provide an effective mechanism to determine, post device implant, whether and to what extend CRT benefits a patient.

Referring again to FIG. 1, as represented by block 109 in some embodiments the prescribed cardiac therapy for the patient may be modified based on an indication as to the effectiveness of the therapy. For example, here it may be determined whether the CRT parameters should be adjusted or whether the CRT should continue to be prescribed for this patient. In addition or alternatively, a new or different medication or a different dosage of medication may be prescribed in an attempt to improve the patient's condition.

Figure 4:
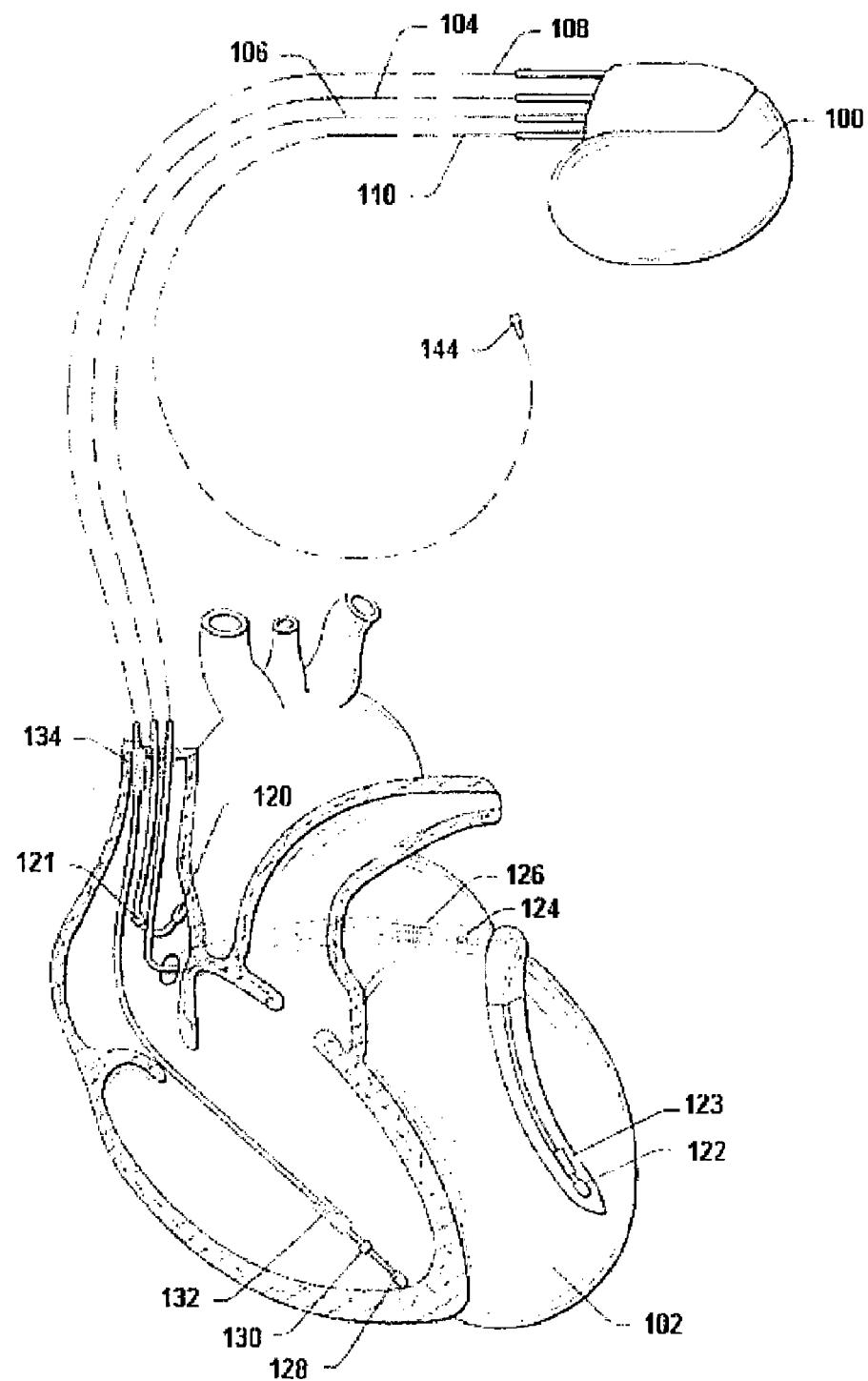
FIG. 4 is a simplified diagram of one embodiment of an implantable stimulation device in electrical communication with at least three leads implanted in a patient's heart for sensing cardiac activity and delivering multi-chamber stimulation and shock therapy.
Figure 5:
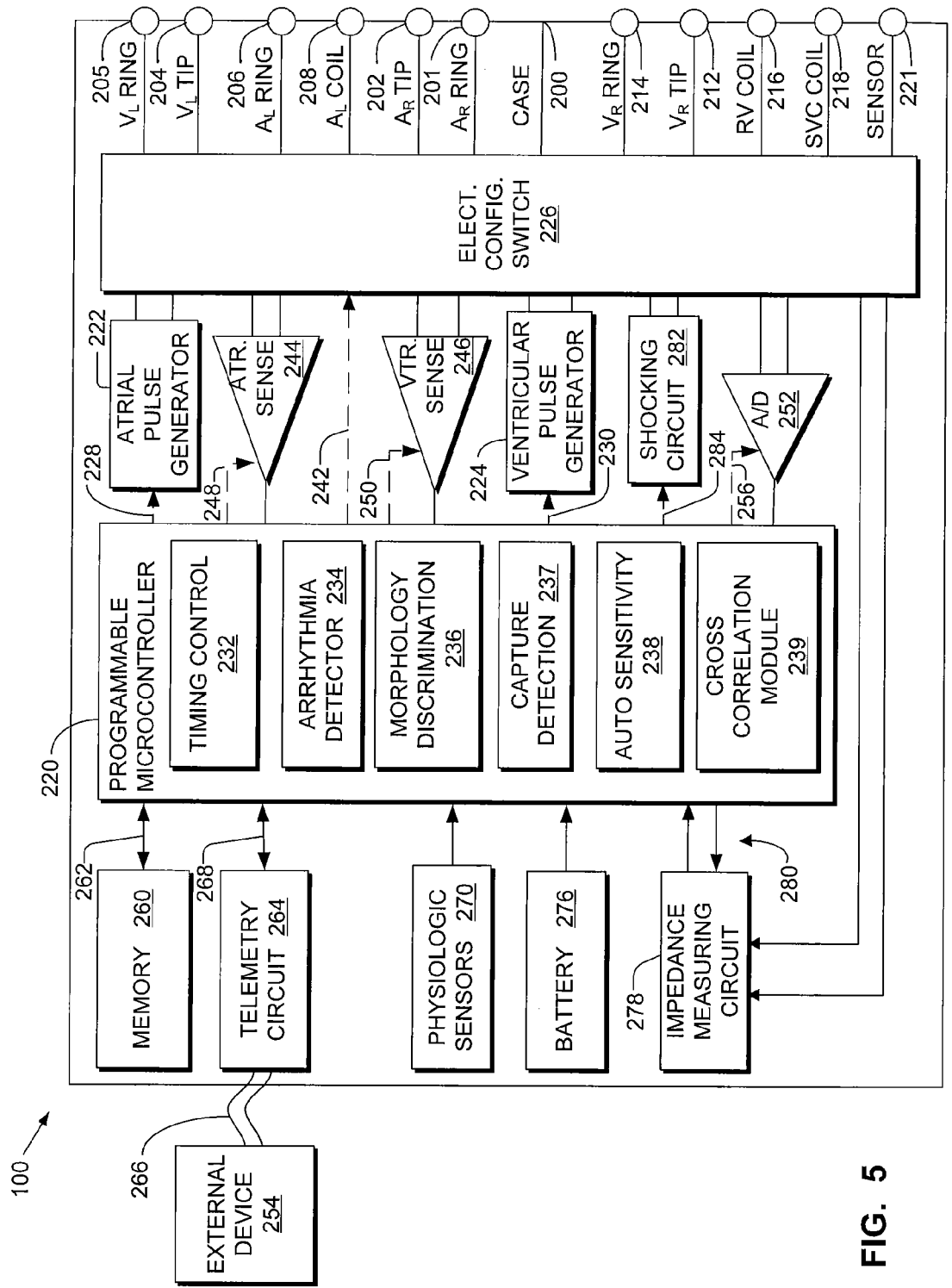
FIG. 5 is a simplified functional block diagram of one embodiment of a multi-chamber implantable stimulation device, illustrating basic elements that are configured to perform therapy assessment and to provide cardioversion, defibrillation or pacing stimulation or any combination thereof.

In some embodiments the acquisition of data and/or the cross correlation of data is performed at least in part by an implantable cardiac device and/or one or more associated components. Referring now to FIGS. 4 and 5, one embodiment of an implantable cardiac device and associated components will be described in some detail.

Exemplary Cardiac Device

The following description sets forth but one exemplary implantable cardiac device (e.g., a stimulation device such as an implantable cardioverter defibrillator) that is capable of being used in connection with the various embodiments that are described herein. It is to be appreciated and understood that other cardiac devices, including those that are not necessarily implantable, can be used and that the description below is given, in its specific context, to assist the reader in understanding, with more clarity, the embodiments described herein.

FIG. 4 shows an exemplary implantable cardiac device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, device 100 is coupled to an implantable right atrial lead 104 having, for example, an atrial tip electrode 120, which typically is implanted in the patient's right atrial appendage or septum. FIG. 4 also shows the right atrial lead 104 as having an optional atrial ring electrode 121.

To sense left atrial and ventricular cardiac signals and to provide left chamber pacing therapy, device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using, for example, a left ventricular tip electrode 122 and, optionally, a left ventricular ring electrode 123; provide left atrial pacing therapy using, for example, a left atrial ring electrode 124; and provide shocking therapy using, for example, a left atrial coil electrode 126 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

Device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Device 100 is also shown in electrical communication with a lead 110 including one or more components 144 such as a physiologic sensor. The lead 110 may be positioned in, near or remote from the heart.

It should be appreciated that the device 100 may connect to leads other than those specifically shown. In addition, the leads connected to the device 100 may include components other than those specifically shown. For example, a lead may include other types of electrodes, sensors or devices that serve to otherwise interact with a patient or the surroundings.

FIG. 5 shows an exemplary, simplified block diagram depicting various components of the cardiac device 100. The device 100 may be adapted to treat both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

Housing 200 for device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 205, 206, 208, 212, 214, 216 and 218

(shown schematically and, for convenience, the names of the electrodes to which they are connected are shown next to the terminals). The connector may be configured to include various other terminals depending on the requirements of the device.

To achieve right atrial sensing and pacing, the connector includes, for example, a right atrial tip terminal (AR TIP) 202 adapted for connection to the atrial tip electrode 120. A right atrial ring terminal (AR RING) 201 may also be included and adapted for connection to the atrial ring electrode 121. To achieve left chamber sensing, pacing, and shocking, the connector includes, for example, a left ventricular tip terminal (VL TIP) 204, a left ventricular ring terminal (VL RING) 205, a left atrial ring terminal (AL RING) 206, and a left atrial shocking terminal (AL COIL) 208, which are adapted for connection to the left ventricular tip electrode 122, left ventricular ring electrode 123, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 5 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (A-V) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 may be utilized by the device 100 for determining desirable times to administer various therapies. The detector 234 may be implemented, for example, in hardware as part of the microcontroller 220, or as software/firmware instructions programmed into the device and executed on the microcontroller 220 during certain modes of operation.

Microcontroller 220 may include a morphology discrimination module 236, a capture detection module 237 and an auto sensing module 238. These modules are optionally used to implement various exemplary recognition algorithms and/or methods. The aforementioned components may be implemented, for example, in hardware as part of the microcontroller 220, or as software/firmware instructions programmed into the device and executed on the microcontroller 220 during certain modes of operation.

The electrode configuration switch 226 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 226, in response to a control signal 242 from the microcontroller 220, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 244 and ventricular sensing circuits (VTR. SENSE) 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits 244 and 246 may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., circuits 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or a data acquisition system 252. This information may be used to determine or detect whether and to what degree tissue capture has occurred and to program a pulse, or pulses, in response to such determinations. The sensing circuits 244 and 246, in turn, receive control signals over signal lines 248 and 250 from the microcontroller 2-20 for purposes of controlling the gain, threshold, polarization charge removal circuitry (not shown), and the timing of any blocking circuitry (not shown) coupled to the inputs of the sensing circuits 244 and 246 as is known in the art.

For arrhythmia detection, the device 100 utilizes the atrial and ventricular sensing circuits 244 and 246 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 234 of the microcontroller 220 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 252. The data acquisition system 252 is configured (e.g., via signal line 256) to acquire intracardiac electrogram ("IEGM") signals or other signals, convert the raw analog data into a digital signal, and store the digital signals for later processing and/or telemetric transmission to an external device 254. For example, the data acquisition system 252 may be coupled to the right atrial lead 104, the coronary sinus lead 106, the right ventricular lead 108 and other leads through the switch 226 to sample cardiac signals across any pair of desired electrodes.

The data acquisition system 252 also may be coupled to receive signals from other input devices. For example, the data acquisition system 252 may sample signals from a physiologic sensor 270 or other components shown in FIG. 5 (connections not shown).

The microcontroller 220 is further coupled to a memory 260 by a suitable data/address bus 262, wherein the programmable operating parameters used by the microcontroller 220 are stored and modified, as required, in order to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device and for cross correlation operations.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, a diagnostic system analyzer or some other device. The microcontroller 220 activates the telemetry circuit 264 with a control signal (e.g., via bus 268). The telemetry circuit 264 advantageously allows intracardiac electrograms and status information relating to the operation of the device 100 (as contained in the microcontroller 220 or memory 260) to be sent to the external device 254 through an established communication link 266.

The device 100 can further include one or more physiologic sensors 270. In some embodiments the device 100 may include a "rate-responsive" sensor that may provide, for example, information to aid in adjustment of pacing stimulation rate according to the exercise state of the patient. One or more physiologic sensors 270 (e.g., a pressure sensor) may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators 222 and 224 generate stimulation pulses.

While shown as being included within the device 100, it is to be understood that a physiologic sensor 270 may also be external to the device 100, yet still be implanted within or carried by the patient. Examples of physiologic sensors that may be implemented in conjunction with device 100 include sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

The one or more physiologic sensors 270 may optionally include sensors to help detect movement (via, e.g., a position sensor) and/or minute ventilation (via an MV sensor) in the patient. Signals generated by the position sensor and MV sensor may be passed to the microcontroller 220 for analysis in determining whether to adjust the pacing rate, etc. The microcontroller 220 may thus monitor the signals for indications of the patient's position and activity status, such as whether the patient is climbing up stairs or descending down stairs or whether the patient is sitting up after lying down. A sensor 270 also may be used to generate activity information for a cross correlation operation.

The device 100 additionally includes a battery 276 that provides operating power to all of the circuits shown in FIG. 5. For a device 100 which employs shocking therapy, the battery 276 is capable of operating at low current drains (e.g., preferably less than 10 µA) for long periods of time, and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium or other suitable battery technology.

The device 100 can further include magnet detection circuitry (not shown), coupled to the microcontroller 220, to detect when a magnet is placed over the device 100. A magnet may be used by a clinician to perform various test functions of the device 100 and/or to signal the microcontroller 220 that the external device 254 is in place to receive data from or transmit data to the microcontroller 220 through the telemetry circuit 264.

The device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 100 has been implanted; measuring stroke volume; and detecting the opening of heart valves, etc. The impedance measuring circuit 278 is advantageously coupled to the switch 226 so that any desired electrode may be used.

In the case where the device 100 is intended to operate as an implantable cardioverter defibrillator ("ICD") device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through, for example, two shocking electrodes and as shown in this embodiment, selected from the left atrial coil electrode 126, the RV coil electrode 132, and/or the SVC coil electrode 134. As noted above, the housing 200 may act as an active electrode in combination with the RV coil electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

CRT Assessment

As mentioned above, the device 100 and associated components such as the leads in FIG. 4 and an external device may be adapted for cross correlation operations. These operations may include, for example, acquiring evoked response data, acquiring activity data, storing data, performing cross correlation operations, outputting indications resulting from an assessment and adjusting therapy.

Electrodes on one or more of the leads in FIG. 4 or other suitable components may be used to sense cardiac signals. Circuitry in the device 100 discussed above may convert these signals to IEGM data and store the IEGM data in the memory 260. A portion of the IEGM data may be tagged or separately stored as necessary for use by the cross correlation process. The data for cross correlation also may be stored, for example, in the memory 260.

The device 100 may be adapted to acquire patient activity data via one or more sensors (e.g., sensors 270 or other sensors) or some other suitable component. For example, an implantable or other sensor (not shown) may sense physiologic or other conditions and generate corresponding signals. Such a sensor may comprise, for example, a sensor to measure movement (e.g., an accelerator to measure acceleration or other motion) of the patient, a pressure sensor to measure changes in pressure associated with activity, a sensor that measures the patient's respiration (e.g., rate or intensity), or any other suitable sensor. The signals generated by the sensor may be sent to the device 100 via one or more terminals (e.g., terminal 221). Circuitry in the device 100 (e.g., switch 226, system 252 and microcontroller 220) may convert the signals to data to be used in the cross correlation operation.

The device 100 also may be adapted to receive patient activity data from a remote device (e.g., as represented generically by external device 254 in FIG. 5). For example, data relating to observed information (e.g., relating to NYHA or 6 MW) may be entered into an external device and downloaded into the device 100 via the telemetry circuit 264.

The microcontroller 220 may be adapted to process the received raw signal data as necessary to generate data for cross correlation operations. For example, a cross correlation module 239 may convert the raw signal data to physical data (e.g., a relative acceleration or pressure value). In addition, the module 239 may average or otherwise condition the received data to provide a more accurate representation of the sensed signal. Also, the module 239 may include, implement or cooperate with a mechanism such as a timer (e.g., timing control 232) to acquire data at desired intervals. Furthermore, the module 239 may store the data in the memory 260 and manage the data to facilitate subsequent retrieval of the data for cross correlation operations.

The module 239 also may be adapted to perform the cross correlation operations. For example, the module 239 may include, implement or cooperate with a mechanism such as a timer to perform the cross correlation at desired intervals. In addition, the module may perform a cross correlation operation as set forth in EQUATION 1 or an otherwise suitable operation.

$$XCORR_{(d)} = \sum_{i=1}^{N} A_{i-d} \cdot B_i \qquad \text{EQUATION 1}$$

The module 239 may be adapted to further process an initial cross correlation result. For example, the module 239 may compute a running average of the cross correlation value and store that result in the memory 260. The module 239 also may analyze the data to identify any trends in the data. Also, the module 239 may format the data in a form suitable for transmission to an external device and/or presentation to a treating physician. The external device may then provide the results to, for example, the physician (e.g., via a download, a display or a printout) or send the results to another device.

Moreover, in some embodiments the module 239 and/or the controller 220 may be adapted to adjust therapy for the patient. For example, cardiac timing parameters (e.g., A-V delay, V-V delay, etc.) and any other LV or RV pacing parameters configured into the device 100 may be modified here. Typically this may be accomplished, for example, in response to an external command from a physician. Alternatively the modification may be invoked automatically based on, for example, a predefined set of actions that may be taken based on certain results (e.g., trends) of the cross correlation operation.

The module 239 also may cooperate with an external device to perform one or more of these operations. For example, the module 239 may send data in any of the various forms herein to an external device so that the external device may perform some of the data operations discussed herein. In addition, the module 239 may operate on data received from an external device. For example, the module 239 may receive data relating to observation of the patient (e.g., 6 MW or NYHA data) and cross correlate this data with the evoked response data. Alternatively, the module 239 may receive global positioning system ("GPS") information that may be used to track a distance traveled by the patient during a six minute walk or other activity. For example, a GPS receiver (implanted in or carried by the patient) may receive GPS signals and send derived coordinates or distance traveled information to the module 239. In other embodiments, a device (implanted in or carried by the patient) may measure the number of steps or gait of the patient during a six minute walk or other activity. This information may then be processed to obtain, for example, a distance covered by the patient.

It should be appreciated that the circuitry and/or functions of the cross correlation module 239 may be implemented in a variety of ways. For example, some of the functionality may be implemented via executable code executing on a programmable device, or be implemented using a hardware state machine, independent computational components or any other suitable circuitry and/or code.

Figure 6:
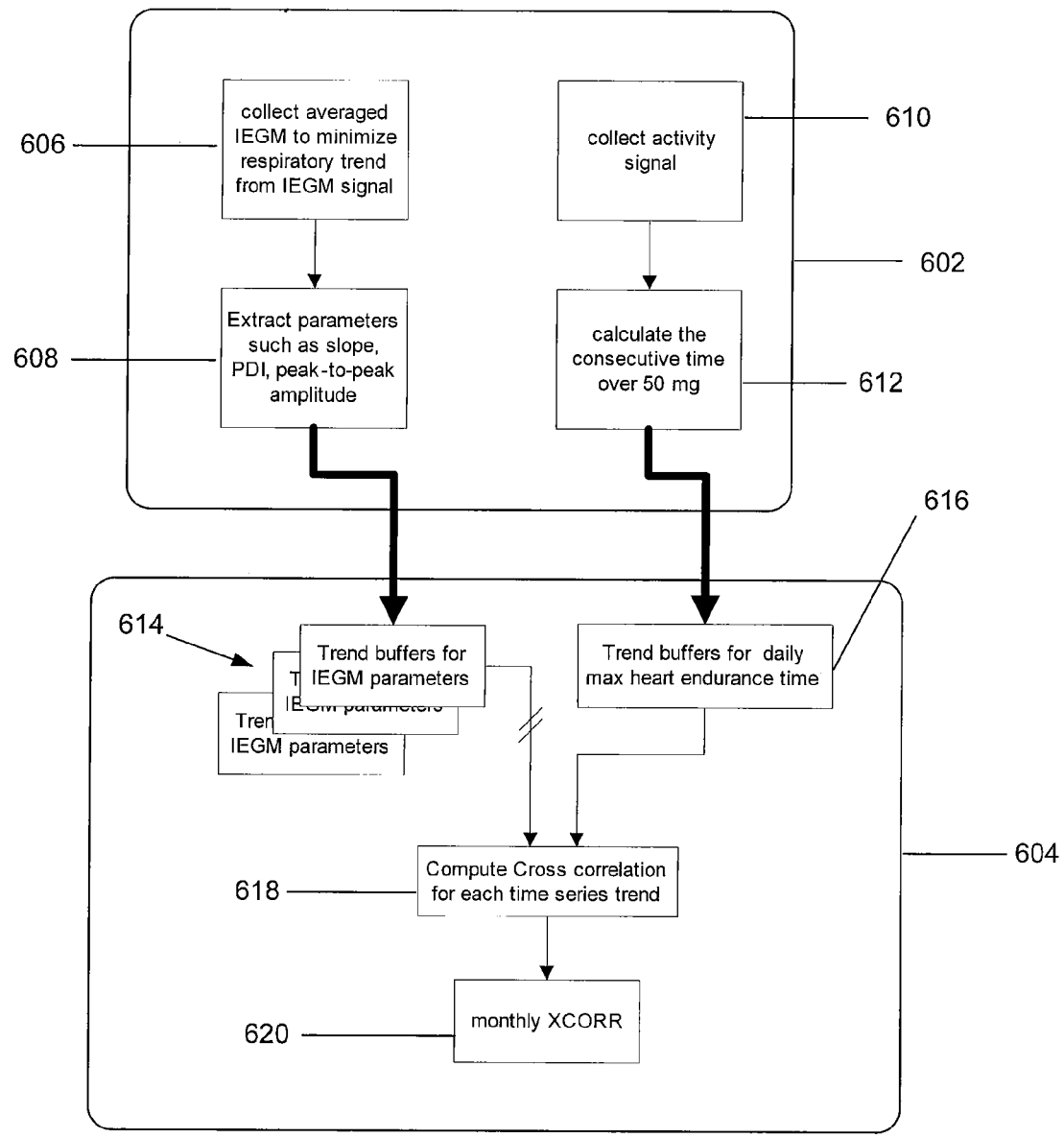
FIG. 6 is a simplified diagram of one embodiment of operations that may be performed to generate cross correlation data.

Referring now to FIG. 6, one embodiment of a CRT assessment technique will be described. These operations may be performed, for example, by the components described herein or by other suitable components. Block 602 relates to data collection operations that are performed on a repetitive (e.g., periodic) basis. For example, these operations may be performed once a day. Block 604 relates to cross correlation operations that may be performed on a less frequent basis. For example, the operations in this block may be performed once a month.

As represented by block 606, IEGM data may be collected once a day for the cross correlation operation. In some embodiments the normal IEGM collection of the device 100 as discussed above may be altered for data collection here. For example, blanking periods or other criteria may be temporarily ignored in the event such an adaptation improves the accuracy of the data collection process or provides some other advantage.

In some embodiments, the data collection may take place when the patient is relatively inactive. For example, the data may be acquired when the patient is sleeping. In this way, the collected data may not be affected by any patient activity (e.g., strenuous activity) that may otherwise significantly impact the IEGM data in a non-deterministic manner. Various techniques may be employed to verify that the patient is inactive. For example, activity sensors as discussed herein may be employed. Alternatively, the data collection may be triggered based on a time of day, a patient generated signal or any other suitable input signal.

In some embodiments averaged IEGM data is collected. For example, to reduce the effect of the patient's respiration on the IEGM signal, several IEGM signal samples may be collected and an average calculated based on these samples.

As represented by block 608 one or more parameters may be extracted from the collected IEGM data. As discussed above, such parameters may include slope, PDI, peak-to-peak amplitude or any other suitable parameter. In addition, it should be appreciated that other information relating to the evoked response may be collected for the cross correlation procedure.

As represented by block 610, activity data may be collected once a day for the cross correlation operation. In some embodiments, data may be collected continually or repeatedly (e.g., randomly or at intervals) until certain forms or values of data are identified. In some embodiments the collection process is adapted to acquire data that is particularly indicative of the patient's capacity to engage in physical activity. For example, signals from an accelerometer may be monitored to determine one or more of: when the patient is engaged in strenuous activity; the strenuousness of the activity; and the length of time the patient is able to engage in the strenuous activity.

As represented by block 612, some embodiments utilize a physical activity surrogate that is based on the length of time a patient maintains a strenuous level of activity. For example, maximum heart endurance time parameters may be obtained by having the patient attempt to exercise very hard on a regular basis (e.g., once a day). As the patient's condition improves, the patient will be able to engage in the activity for subsequently longer and longer periods of time.

In some embodiments an accelerometer may be used to calculate how long a person continually engages in activity that results in a reading of 50 mg or more (one example of a threshold indicating a high level of activity). Here, the activity-related circuitry may be adapted to trigger a timer when the activity level results in a reading of approximately 50 mg or higher. The timer may then remain activated until the activity level drops to a level resulting in an accelerometer reading of less than 50 mg. The total time at or above 50 mg or some parameter based on this information may then be used for the cross correlation.

In some embodiments an adaptive threshold may be used to gauge a patient's activity level. For example, if a patient's condition worsens, a reading of 50 mg may not be readily attainable by the patient. Accordingly, the threshold may be reduced (one or more times) if such a condition persists over a period of time. Alternatively, in some cases the threshold may be increased in accordance with the patient's condition or some other factor.

Referring now to block 604, the data collected on a daily basis at block 602 is stored in one or more trend buffers (e.g., in memory 260). Specifically, the evoked IEGM-based data is stored in trend buffers 614 and the activity-based data is stored in trend buffers 616.

As represented by block 618, on a monthly basis a cross correlation is performed over the data in the trend buffers. For example, a cross correlation may be performed between thirty IEGM parameters (e.g., peak-to-peak value) and thirty activity parameters (e.g., time over 50 mg).

As represented by block 620, the monthly cross correlation data may be processed and stored for later use. In some embodiments a running average of the cross correlation data may be computed and stored in the memory 260. The above process may then be repeated to generate a series of cross correlation entries.

Figure 7:
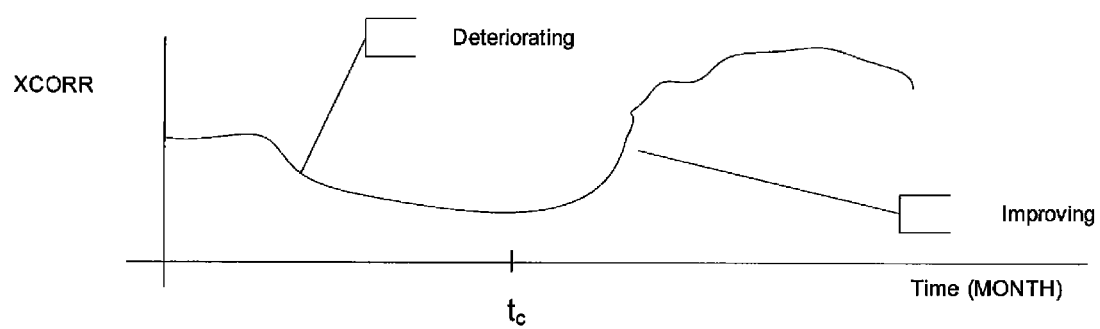
FIG. 7 is a simplified graph illustrating an example of a trend in cross correlation data.

As discussed above, once a cross correlation series of a desired size is acquired, the series may then be assessed, e.g., by performing a trend analysis. FIG. 7 illustrates one embodiment of a hypothetical graph of a cross correlation series. It may be seen that in a first portion (e.g., before $t_c$) of the graph, the cross correlation parameter ("XCORR") is decreasing. Accordingly, an indication of a deteriorating patient condition may be generated upon assessment of this information. After modification of the therapy at time $t_c$ in response to the negative indication, the cross correlation parameter is shown as increasing. Accordingly, an indication of an improving patient condition may then be generated.

In view of the above, it should be appreciated that cross correlation may be effectively applied to assess cardiac therapy such as CRT. Moreover, it should be appreciated based on the teachings herein that this may be accomplished in a variety of ways other than those specifically set forth herein. For example, various operation timings other than those set forth herein may be employed. In addition, other forms of cross correlation or other suitable operations may be used to assess therapy. Furthermore, such operations may operate on types of data or information beyond those specifically mentioned here. For example, other types of data may be used to indicate cardiac performance and/or patient activity. In addition, in some embodiments cross correlation may be performed between (e.g., in multiple operations) three or more types of data.

The various structures and functions described herein may be incorporated into a variety of apparatuses (e.g., a stimulation device, a lead, a monitoring device, etc.) and implemented in a variety of ways. Different embodiments of the stimulation device may include a variety of hardware and software processing components. In some embodiments, hardware components such as processors, controllers, state machines and/or logic may be used to implement the described components or circuits. In some embodiments, code such as software or firmware executing on one or more processing devices may be used to implement one or more of the described functions or components.

The components and functions described herein may be connected and/or coupled in many different ways. The manner in which this is done may depend, in part, on whether and how the components are separated from the other components. In some embodiments some of the connections and/or couplings represented by the lead lines in the drawings may be in an integrated circuit, on a circuit board or implemented as discrete wires or in other ways.

The signals discussed herein may take several forms. For example, in some embodiments a signal may comprise electrical signals transmitted over a wire, light pulses transmitted through an optical medium such as an optical fiber or air, or RF waves transmitted through a medium such as air, etc. In addition, a plurality of signals may be collectively referred to as a signal herein. The signals discussed above also may take the form of data. For example, in some embodiments an application program may send a signal to another application program. Such a signal may be stored in a data memory.

While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A method of assessing effectiveness of cardiac therapy, comprising:
    delivering cardiac resynchronization pacing pulses to left and right ventricles of a patient's heart to control synchronization of contractions of the left and right ventricles;
    collecting an evoked response from an intracardiac electrogram (IEGM) of the left and right ventricles in response to the delivered pacing pulses;
    extracting one or more parameters from the collected evoked response;
    collecting data associated with activity of the patient; and
    cross correlating the one or more parameters extracted from the evoked response and the collected activity data to generate an indication of effectiveness of the cardiac resynchronization pulses delivered to the left and right ventricles.

2. The method of claim 1 wherein the one or more extracted parameters comprises peak-to-peak intracardiac electrogram data.

3. The method of claim 2 comprising averaging a plurality of samples of the peak-to-peak intracardiac electrogram data to provide the evoked response data.

4. The method of claim 1 wherein the one or more extracted parameters comprises paced depolarization integral data.

5. The method of claim 1 wherein the one or more extracted parameters is indicative of a slope of an intracardiac electrogram signal.

6. The method of claim 1 wherein the activity data comprises patient acceleration data.

7. The method of claim 1 wherein the activity data comprises a maximum heart endurance time.

8. The method of claim 1 comprising monitoring patient activity signals to determine an amount of time the patient maintains a level of activity above a threshold level.

9. The method of claim 1 wherein the activity data comprises a time associated with a continuous accelerometer reading of at least approximately 50 mg.

10. The method of claim 1 wherein the activity data comprises a distance associated with a timed activity.

11. The method of claim 1 wherein the activity data is generated in accordance with a subjective patient evaluation.

12. The method of claim 1 wherein the evoked response data and the activity data are collected periodically.

13. The method of claim 1 comprising generating a moving average of a cross correlation result to generate the indication.

14. The method of claim 1 comprising collecting the evoked response data when the patient is inactive.

15. The method of claim 1 comprising collecting the evoked response data when the patient is asleep.

16. The method of claim 1 comprising collecting the evoked response data in accordance with a measured of activity level of the patient.

17. An apparatus adapted to assess effectiveness of cardiac therapy, comprising:
    a pulse generator adapted to deliver cardiac resynchronization pacing pulses to left and right ventricles of a patient's heart to control synchronization of contractions of the left and right ventricles;
    an evoked response circuit adapted to obtain data associated with an evoked response from an intracardiac electrogram of a patient in response to the delivered cardiac resynchronization pacing pulses and to extract one or more parameters from the evoked response data;
    an activity level circuit adapted to obtain data associated with activity of the patient; and
    a cross correlator adapted to cross correlate the one or more extracted parameters and the activity data to generate an indication of effectiveness of the delivered cardiac resynchronization pacing pulses.

18. The apparatus of claim 17 wherein:
    the evoked response circuit and the activity level circuit are adapted to repeatedly collect the evoked response data and the activity data, respectively, over time; and
    the cross correlator is adapted to perform the cross correlation at specified times, wherein the cross correlation is performed over the evoked response data and the activity data collected substantially between the specified times.

19. The apparatus of claim 17 wherein at least a portion of the apparatus is implemented within an implantable cardiac device.

20. An implantable system comprising:

means for delivering cardiac resynchronization pacing pulses to left and right ventricles of a patient's heart to control synchronization of contractions of the left and right ventricles;

means for collecting data associated with an evoked response of a patient from an intracardiac electrogram in response to the delivered cardiac resynchronization pacing pulses;

means for extracting one or more parameters from the collected evoked response data;

means for collecting data associated with activity of the patient; and means for cross correlating the one or more parameters and the collected activity data to generate an indication of effectiveness of the delivered cardiac resynchronization pacing pulses.

* * * * *